United States Patent
Kirstgen et al.

(10) Patent No.: US 6,531,149 B1
(45) Date of Patent: Mar. 11, 2003

(54) ESTRADIOL-CONTAINING PATCH FOR TRANSDERMAL APPLICATION OF HORMONES

(75) Inventors: Elvira Kirstgen, Neuwied (DE); Reinhold Meconi, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/744,711

(22) PCT Filed: Jul. 16, 1999

(86) PCT No.: PCT/EP99/05085
§ 371 (c)(1), (2), (4) Date: Apr. 1, 2001

(87) PCT Pub. No.: WO00/06131
PCT Pub. Date: Feb. 10, 2000

(30) Foreign Application Priority Data

Jul. 29, 1998  (DE) .......................................... 198 34 007

(51) Int. Cl.⁷ .......................... A61K 9/70; A61L 15/16; A61F 13/02; A01N 25/34
(52) U.S. Cl. ...................... 424/449; 424/443; 424/402; 424/447; 424/448
(58) Field of Search ................................ 424/402, 443, 424/447, 448, 449; 514/847

(56) References Cited

U.S. PATENT DOCUMENTS

| | | | |
|---|---|---|---|
| 4,624,665 A | | 11/1986 | Nuwayser |
| 4,695,465 A | * | 9/1987 | Kigasawa et al. .......... 424/449 |
| 5,948,433 A | * | 9/1999 | Burton et al. ................ 424/448 |

FOREIGN PATENT DOCUMENTS

| | | |
|---|---|---|
| DE | 2006696 | 9/1970 |
| DE | 2006969 | 10/1970 |
| DE | 3205258 | 9/1982 |
| DE | 251567 | 11/1987 |
| DE | 3743946 | 3/1989 |
| DE | 4416927 | 8/1995 |
| EP | 0186019 | 7/1986 |
| EP | 0275716 | 7/1988 |
| EP | 0285563 | 10/1988 |
| EP | 0328806 | 8/1989 |
| EP | 0787488 | 8/1997 |
| WO | WO 87/07138 | 12/1987 |
| WO | 9619976 | 7/1996 |

* cited by examiner

Primary Examiner—Thurman K. Page
Assistant Examiner—Humera N. Sheikh
(74) Attorney, Agent, or Firm—Jordan & Hamburg LLP

(57) ABSTRACT

An active substance-containing patch for controlled release of estradiol or its pharmaceutically acceptable derivatives, alone or in combination with gestagens, to the human or animal skin, consisting of a backing layer, an active substance-containing reservoir connected thereto which is suitable for combined active substance release and which has been produced using pressure-sensitive adhesives, and a detachable protective layer, is characterized in that the pressure-sensitive adhesive contains wool wax or components thereof and zinc oxide.

11 Claims, No Drawings

ESTRADIOL-CONTAINING PATCH FOR TRANSDERMAL APPLICATION OF HORMONES

The invention relates to an active substance-containing patch for controlled release of estradiol or its pharmaceutically acceptable derivatives, alone or in combination with gestagens, to the human or animal skin.

Estrogen-and/or gestagen-containing patches are already known. They do, however, have disadvantages in that they either contain ethanol or involve the potential danger of the active substance recrystallizing in the course of time.

From DE-OS 32 05 258 and EP 0 285 563 it is known to simultaneously administer estradiol and ethanol in a patch formulation. The production of this patch is, however, very complicated, and the patches have little wearing comfort after they have been applied, since they lack flexibility.

EP 0 285 563 describes a transdermal therapeutic system for the combined application of estrogens and gestagens. The reservoir contains the active substance formulation and optionally a membrane, as well as ethanol as percutaneous, absorption-enhancing agent. Since the release of active substance is mainly controlled by the membrane, this transdermal therapeutic system is fundamentally different from the active substance patch according to the present invention. In the patch described by this document, the adhesive merely has the function of fixing the patch on the skin. The fact that it is capable of contributing to the control of the active substance release does not constitute its main task, but is merely a—possibly even unwanted—side effect. The patch is a so-called "pouch patch", since the active substance formulation is present within a pouch, consisting of an impermeable backing layer and a membrane with adhesive layer. As a consequence of its complicated structure, the production of this patch requires great expenditure since the individual components must be prepared separately and then, in a further process step, combined to form a patch.

EP 0 275 716 describes a transdermal two-layer system—in contrast to the mono-layer system of the present invention—for simultaneous administration of one or more estrogens, which are dissolved or microdispersed in the polymer layer. Here, the pressure-sensitive layer contains, apart from the active compounds, substances which enhance transdermal absorption. Polymer and pressure-sensitive layers may consist of polyacrylates, silicones or polyisobutylenes.

EP 0 328 806 describes a membrane-free transdermal therapeutic system the matrix of which consists of a polyacrylate adhesive, a solvent, a penetration enhancer and estrogens, its derivatives and combinations thereof.

WO 87/07138 describes an estradiol patch comprising a backing layer, a matrix containing the active substance, and a pressure-sensitive adhesive, which adhesive is covered by a removable protective layer. The production of the matrix and pressure-sensitive adhesive is carried out in process steps requiring a great expenditure in terms of the technology to be applied, by homogenizing, degasifying, coating, drying and separating into individual pieces. In one embodiment, the backing layer must even be coated with a pressure-sensitive adhesive, which means a further process step. The combining of the individual parts takes place in a separate process step. The overall production of the patch thus involves great expenditure and is complicated.

From U.S. Pat. No. 4,624,665, systems are known which contain the active substance in microencapsuled form in the reservoir. The reservoir is embedded between a backing layer and a membrane. The outer margin of the system is provided with a pressure-sensitive adhesive. The structure and production of this system is very complicated since the active substance must be microencapsulated and distributed in a homogenous phase, which then, in further process steps, must be embedded between backing layer and membrane. In addition, the system must then be provided with an adhesive margin and covered with a protective layer.

Further, from EP 0 186 019 active substance patches are known wherein to a rubber/adhesive resin mass are added water-swellable polymers, and from which patches estradiol can be released. It has, however, emerged that the release of estradiol from these active substance patches is too low by far and does not meet therapeutic requirements.

In DE-OS 20 06 696 a patch or an adhesive bandage is described which has systematic action and wherein contraceptive substances are incorporated in the adhesive component or the adhesive film. The adhesive film may be an acrylate.

It is thus the object of the present invention to avoid the above-mentioned disadvantages and to provide a stable, i.e. recrystallization-free, estrogen-and/or gestagen-containing patch having sufficient active substance release, whose release is not subject to change by storage.

Surprisingly, it has emerged that this object is achieved by an estrogen-and/or gestagen-containing pressure-sensitive adhesive which contains wool wax, also known as lanolin wax, or constituents thereof and zinc oxide.

The above-described object is thus achieved by an active substance-containing patch according to the main claim. The subclaims relate to especially preferred embodiments of the subject matter of the invention.

Wool wax is known as a pharmaceutical raw material and is described as such by the pharmacopoeias. It is used because of its liberating capacity for active substances, its being well tolerated by the skin and its absorption capacity for water.

Zinc oxide is also described in the pharmacopoeias. Zinc oxide acts as a mild disinfectant and is antiphlogistic, furthermore it reacts faintly alkaline.

The active substance patch according to the invention can be used for cosmetic as well as therapeutic purposes in human and veterinary medicine.

The recrystallization-free estrogen-and/or gestagen-containing patch having sufficient active substance release contains in its reservoir estradiol and its pharmaceutically acceptable derivatives, alone or in combination with gestagens, in a concentration of a total of 1–20%-wt., relative to the totality of the reservoir components, in fact in a molar ratio of 1:1 to 1:10.

The estradiol-containing reservoir may contain at least one component belonging to the group comprising age-protecting agents, plasticizers, antioxidants and absorption enhancers. Suitable plasticizers are known to those skilled in the art, and are described, for example, in DE 37 43 946. The estradiol-containing reservoir usually contains plasticizers in a portion of up to 5%-wt.

Furthermore, the reservoir contains age-protecting agents in a concentration of up to 1%-wt. These are known to those skilled in the art and are described, for example, in DE 37 43 946.

The materials for the impermeable backing layer and the detachable protective layer are also known to those skilled in the art.

The estradiol-containing reservoir may be made from the solution, dispersion and from the melt.

In case the reservoir has no sufficient inherent tack on the skin, it can be provided with an additional active substancefree pressure-sensitive adhesive or with a circumferential pressure-sensitive adhesive margin. In this way it is ensured that the transdermal patch adheres on the skin over the entire period of application.

A particularly preferred structure of the transdermal estradiol-containing patch is a matrix system, wherein, as is known, the matrix takes over the control of the active substance release and is subject to the √t-law according to Higuchi. This does not mean, however, that a membrane system is not of advantage in special cases. In membrane systems, an active substance release-controlling membrane is located between reservoir and pressure-sensitive adhesive layer.

The thickness of the transdermal patch is dependent on the therapeutic requirements and can be adjusted accordingly. Usually, it ranges from 0.03–0.6 mm.

In the following, the invention will be illustrated by way of embodiment examples.

EXAMPLE 1

97.86 g of Durotak 387–2287 solution (50.2 g of solid matter)

4.0 g of wool wax 21.56 g of ethanol and 10.78 g of acetic acid ethyl ester are homogenized by stirring at room temperature for 2 to 3 hours. Subsequently, 2.0 g of estradiol hemihydrate and 7.0 g norethindrone acetate are added and this is stirred for about 1 hour. Theraftor, 16.8 g of zinc oxide are added and this is stirred for a further 30 min.

The resultant active substance-containing adhesive mass is coated on the detachable protective layer (Hostaphan RN 100, coated on one side with silicone —by Hoechst Diafoil) such that an active substance-containing reservoir having a weight per unit area of approximately 80 g/m² results. On this reservoir is laminated the impermeable backing layer (polyester film, 19 μm-thick). Subsequently, active substance patches of 16 cm² are punched out.

EXAMPLES 2 and 3

The preparation is carried out as in Example 1, but with the raw material quantities as stipulated in Table 1 (preparation formula).

For measuring the human skin penetration, the skin is clamped into the Franz cell. An estrogen-and/or gestagen-containing patch having a surface of 1.539 cm² is stuck on this skin and the active substance release is measured at 37° C. (acceptor medium: 0.9% sodium chloride solution +0.1% NaN₃).

The examination on recrystallization phenomena is carried through in counterlight.

The results are listed in Table 2.

TABLE 1

| | Composition (Amounts in g) | | | | |
|---|---|---|---|---|---|
| Example | Durotak 387-2287 solid matter | Wool wax | Zinc oxide | Estradiol hemihydrate | Norethindrone acetate |
| 2 | 50.2 | 5.6 | 15.2 | 2.0 | 7.0 |
| 3 | 50.2 | 2.4 | 18.4 | 2.0 | 7.0 |

TABLE 2

| | Analysis results | | | | |
|---|---|---|---|---|---|
| | Active substance content μg/16 cm² | | Human skin penetration μg/16 cm² (24–48 Std.) | | Recrystallisation |
| Example | Es | NeA | Es | NeA | |
| 1 | 3.200 | 11.200 | 56 | 90 | none |
| 2 | 3.200 | 11.200 | 49 | 76 | none |
| 3 | 3.200 | 11.200 | 48 | 79 | none |
| Comparison product Evorel Conti | 3.200 | 11.200 | 33 | 46 | considerable |

Es: Estradiol hemihydrate
NeA: Norethindrone acetate

As is shown by the Table, with the patch according to the invention one obtains a clearly improved penetration through the human skin as compared to the comparison product. At the same time it can be ascertained that in the examples according to the invention no recrystallization occurs whatsoever.

What is claimed is:

1. Active substance-containing patch for controlled release of hormonal active substance consisting of at least one of estradiol or its pharmaceutically acceptable derivatives, or at least one of estradiol or its pharmaceutically acceptable derivatives and at least one gestagen in a molar ratio of the former to the latter of 1:1 to 1:10, to human or animal skin, comprising a backing layer, an active substance-containing reservoir connected thereto which is suitable for active substance release and which comprises a layer of at least one pressure-sensitive adhesive containing polymer consisting essentially of acrylic polymer, and a detachable protective layer, wherein the acrylic polymer pressure-sensitive adhesive contains said active substance in a concentration of 1–20%-wt. based on the total weight of the reservoir, wool wax or components thereof in a concentration of 1–30%-wt. based on the total weight of the reservoir and zinc oxide in a concentration of 1–30%-wt. based on the total weight of the reservoir.

2. Active substance-containing patch according to claim 1, wherein the reservoir contains at least one component belonging to the group of age-protecting agents, antioxidants and absorption enhancers.

3. Active substance-containing patch according to claim 1, wherein the pressure-sensitive adhesive is a pressure-sensitive solution adhesive, a pressure-sensitive dispersion adhesive or a pressure-sensitive hot-melt adhesive.

4. Active substance-containing patch according to Claim 1, wherein the backing layer is impenneable to the components of the reservoir.

5. Active substance-containing patch according claim 1, wherein the reservoir comprises a plurality of layers including a plurality of active substance-containing pressure-sensitive adhesive layers.

6. Active substance-containing patch according to claim 1, further comprising an active substance release-controlling membrane between the reservoir and the pressure-sensitive adhesive layer.

7. Active substance-containing patch according to claim 1, wherein the reservoir includes a circumferential, pressure-sensitive adhesive margin.

8. Active substance-containing patch according to claim 1, wherein the thickness of the active substance-containing patch is in the range of 0.03–0.6 mm.

9. Active substance-containing patch according to claim 1, wherein said concentration of said active substance is 1.5–15%-wt.

10. Method of treating a human to improve skin of the human cosmetically, comprising applying to said skin said active substance-containing patch according to claim 1.

11. Method of treating skin of a human or an animal therapeutically, comprising applying to said skin said active substance-containing patch according to claim 1.

* * * * *